United States Patent
Beaupre

(10) Patent No.: US 6,660,017 B2
(45) Date of Patent: *Dec. 9, 2003

(54) BALANCED ULTRASONIC BLADE INCLUDING A SINGULAR BALANCE ASYMMETRY

(75) Inventor: Jean M. Beaupre, Cincinnati, OH (US)

(73) Assignee: Ethicon Endo-Surgery, Inc., Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/862,057

(22) Filed: May 21, 2001

(65) Prior Publication Data

US 2002/0077644 A1 Jun. 20, 2002

Related U.S. Application Data

(63) Continuation of application No. 09/441,813, filed on Nov. 17, 1999, now abandoned, which is a continuation of application No. 09/106,028, filed on Jun. 29, 1998, now abandoned.

(51) Int. Cl.$^7$ ............................................. A61B 17/32
(52) U.S. Cl. ................................................... 606/169
(58) Field of Search .............................. 606/169, 170, 606/167; 604/22

(56) References Cited

U.S. PATENT DOCUMENTS

| 2,874,470 A | 2/1959 | Richards |
| 2,990,616 A | * 7/1961 | Balamuth et al. |
| 3,053,124 A | 9/1962 | Balamuth et al. ............... 78/82 |
| 3,086,288 A | 4/1963 | Balamuth et al. |
| 3,526,219 A | 9/1970 | Balamuth ...................... 128/2 |

(List continued on next page.)

FOREIGN PATENT DOCUMENTS

| DE | 203 229 | 12/1983 |
| EP | 0 456 470 A1 | 11/1991 |
| EP | 0 830 845 A1 | 9/1996 |
| GD | 203 229 | 1/1982 |
| WO | WO 86/02257 A1 | 4/1986 |
| WO | WO 93/14709 A1 | 8/1993 |

OTHER PUBLICATIONS

Copy of EPO Search Report.
International Standard IEC 61847, First edition Jan. 1998, Ultrasonics Surgical systems—"Measurement and declaration of the basic output characteristics" ©IEC 1998.
International Electrotechnical Commission, *Ultrasonics – Surgical systems –Measurement and declaration of the basic output characteristics*, First edition, 1998–01, IEC 61847, published in Geneva, Switzerland, pp. 1–31.

Primary Examiner—Michael H. Thaler

(57) ABSTRACT

A balanced ultrasonic surgical instrument is described wherein the balanced ultrasonic surgical instrument includes an ultrasonic transmission rod and an ultrasonically actuated blade attached to the distal end of the ultrasonic transmission rod. According to the present invention, the ultrasonically actuated blade includes a treatment portion and a balance portion. The treatment portion has a functional feature such as, for example, a triangular blade which makes the treatment portion asymmetric. The balance portion includes a singular asymmetric balance feature designed and positioned to balance out any undesirable torque generated by the treatment portion. The balance portion further extends generally from a node point on the ultrasonic transmission rod to the proximal end of the treatment portion.

22 Claims, 8 Drawing Sheets

U.S. PATENT DOCUMENTS

| | | | |
|---|---|---|---|
| 3,830,240 A | 8/1974 | Antonevich et al. | 128/328 |
| 3,861,391 A | 1/1975 | Antonevich et al. | 128/328 |
| 3,990,452 A | 11/1976 | Murry et al. | 128/305 |
| 4,136,700 A | 1/1979 | Broadwin et al. | 128/305 |
| 4,169,984 A | 10/1979 | Parisi | 310/323 |
| 4,283,175 A | 8/1981 | Nash | |
| 4,526,571 A | 7/1985 | Wukchinich | 604/22 |
| 4,634,419 A | 1/1987 | Kreizman et al. | 604/22 |
| 4,911,161 A | 3/1990 | Schechter | 606/171 |
| 4,920,954 A | 5/1990 | Alliger et al. | 128/24 |
| 4,974,581 A | 12/1990 | Wiksell | 128/24 A |
| 4,992,048 A | 2/1991 | Goof | 433/102 |
| 5,019,083 A | 5/1991 | Klapper et al. | 606/99 |
| 5,047,008 A | 9/1991 | de Juan, Jr. et al. | 604/22 |
| 5,047,043 A | 9/1991 | Kubota et al. | 606/169 |
| 5,180,363 A | 1/1993 | Idemoto et al. | 202/32 |
| 5,188,102 A | 2/1993 | Idemoto et al. | 128/24 AA |
| 5,205,817 A | 4/1993 | Idemoto et al. | 604/22 |
| 5,221,282 A | 6/1993 | Wuchinich | 606/99 |
| 5,222,937 A | 6/1993 | Kagawa | 604/22 |
| 5,248,296 A | 9/1993 | Alliger | 609/22 |
| 5,312,329 A | 5/1994 | Beaty et al. | 604/22 |
| 5,318,570 A | 6/1994 | Hood et al. | 606/99 |
| 5,322,055 A | 6/1994 | Davison et al. | 601/2 |
| 5,324,297 A | 6/1994 | Hood et al. | 606/99 |
| 5,324,299 A | 6/1994 | Davison et al. | 606/167 |
| 5,397,293 A | 3/1995 | Alliger et al. | 601/2 |
| 5,413,578 A | 5/1995 | Zahedi | 606/86 |
| 5,417,654 A | 5/1995 | Kelman | 604/22 |
| 5,480,379 A | 1/1996 | La Rosa | 604/22 |
| 5,531,597 A | 7/1996 | Foulkes et al. | 433/119 |
| 5,653,724 A | 8/1997 | Imonti | 606/169 |
| 5,669,922 A * | 9/1997 | Hood | 606/169 |
| 5,676,649 A | 10/1997 | Boukhny et al. | 604/22 |
| 6,024,750 A | 2/2000 | Mastri et al. | 606/169 |

* cited by examiner

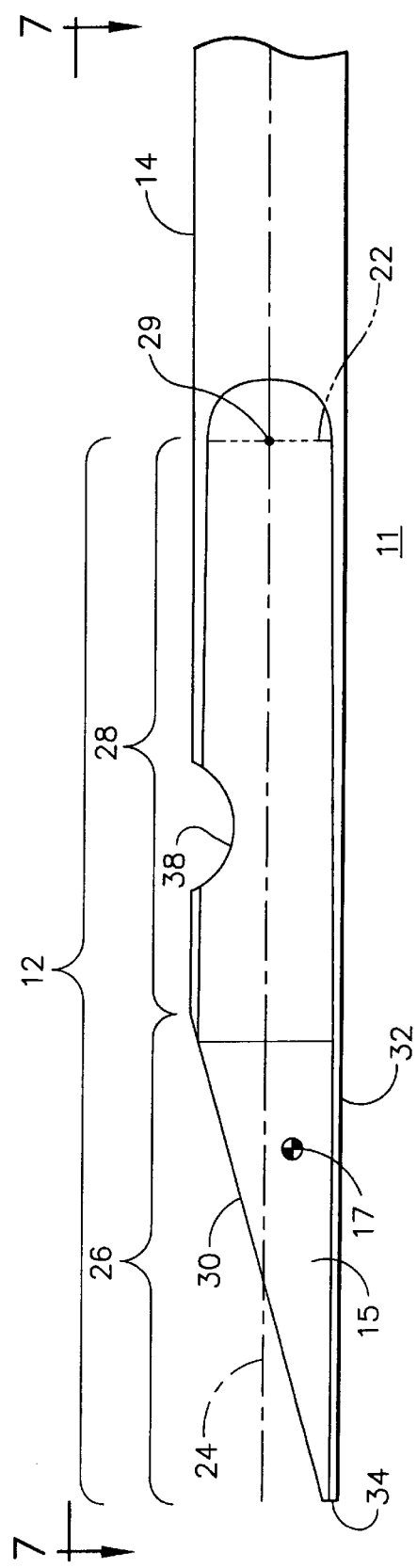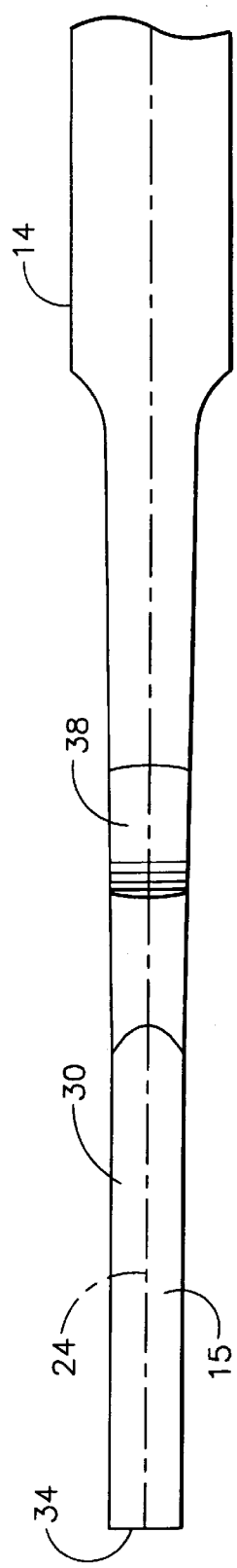

BALANCED ULTRASONIC BLADE INCLUDING A SINGULAR BALANCE ASYMMETRY

CROSS REFERENCE TO RELATED APPLICATIONS

This application is a continuation of prior application Ser. No. 09/441,813, filed on Nov. 17, 1999, abandoned, which is a continuation of prior pending application Ser. No. 09/106,028, filed on Jun. 29, 1998, abandoned.

This application is related to the following co-pending patent applications: application Ser. No. 09/106,686; application Ser. No. 09/106,415; application Ser. No. 09/106,661, which are hereby incorporated herein by reference.

FIELD OF THE INVENTION

The present invention relates, in general, to curved ultrasonic blades for use in surgical instruments and, more particularly, to balanced curved ultrasonic blade including a singular balance asymmetry.

BACKGROUND OF THE INVENTION

Ultrasonic instruments are often used in surgery to cut and coagulate tissue. Exciting the end effector (e.g. cutting blades) of such instruments at ultrasonic frequencies induces longitudinal vibratory movement which generates localized heat within adjacent tissue, facilitating both cutting and coagulation. Because of the nature of ultrasonic instruments, a particular ultrasonically actuated end effector may be designed to perform numerous functions, including, for example, cutting and coagulation. The structural stress induced in such end effectors by vibrating the blade at ultrasonic frequencies may have a number of undesirable effects. Such undesirable effects may include, for example, substantial transverse motion in the instrument waveguide which may lead to, for example, excess heat generation in the waveguide or premature stress failure. The undesirable effects of vibrating a surgical end effector at ultrasonic frequencies are compounded where the end effector is not symmetrical, that is, where the mass of the end effector is not distributed symmetrically about a line extending through the central axis of the transmission waveguide. Therefore, one way to improve the performance of ultrasonically actuated end effectors is to design end effectors which are substantially symmetric about the central axis of the transmission waveguide. Alternatively, the surgical end effector may be small and short, in which case the end effector will act like a small lumped mass at the end of the transmission waveguide and will not induce substantial transverse motion in the waveguide. Where it is desirable to design end effectors which are not symmetric, performance may be improved by designing the end effector such that the center of mass of the end effector is located along a line which extends through the central axis of the waveguide. One known method of moving the center of mass is to add or subtract mass opposite or close to the asymmetric region until the center of mass lies along a central axis. As a further alternative, longitudinal vibratory motion in the waveguide may be reduced or eliminated by using thicker, more robust waveguides which are not as subject to transverse vibratory motion. However, the use of thick waveguides may not be an acceptable alternative where the ultrasonic surgical instrument is being designed for use in minimally invasive surgery such as endoscopic or laparoscopic surgery. In such instruments it is generally desirable to reduce the diameter of the ultrasonic waveguide in order to fit the instrument through the tiny surgical incisions, narrow body orifices and through trocars presently being used and being designed for future procedures. Long thin ultrasonic waveguides, such as those used in instruments for minimally invasive surgery, are particularly susceptible to transverse vibrations introduced by imbalances in the end effector.

For certain applications, it is desirable to include one or more axially asymmetrical features (e.g. a triangular blade), to enhance performance of the end effector. It may also be desirable to design such end effectors to be relatively long, in order to facilitate certain surgical procedures. In such end effectors, it is not always possible or desirable to include opposed balancing features in the treatment portion in order to balance the end effector by aligning the center of mass with the central axis of the transmission waveguide. It would, therefore, be desirable to design an ultrasonic surgical instrument including a waveguide and an ultrasonic end effector wherein undesirable transverse vibrations resulting from the inclusion of beneficial asymmetrical features (e.g. a triangular blade) in the working portion of the end effector have been reduced or eliminated. It would further be advantageous to design such an instrument wherein the undesirable transverse vibrations have been reduced or eliminated without adding balancing features to the treatment portion of the end effector. It would further be advantageous to design an end effector wherein undesirable transverse vibrations resulting from the inclusion of beneficial asymmetrical features in the treatment portion of the end effector have been reduced or eliminated by adding an asymmetrical balancing feature proximal to the treatment portion of the end effector. It would further be advantageous to design an asymmetric end effector with a center of mass which is not on the central axis of the transmission waveguide wherein significant transverse motion is not induced in the waveguide by the asymmetric end effector.

SUMMARY OF THE INVENTION

A balanced ultrasonic surgical instrument including an ultrasonic transmission rod and an ultrasonically actuated blade attached to the distal end of the ultrasonic transmission rod. According to the present invention, the ultrasonically actuated blade includes a treatment portion and a balance portion. The treatment portion has a functional feature such as, for example, a triangular ultrasonic blade which makes the treatment portion asymmetric. Such a functional feature may be referred to as a functional asymmetry. The balance portion includes a singular asymmetric feature designed and positioned to balance out any undesirable torque generated by the treatment portion. Such balance feature may be referred to as balance asymmetry and may include asymmetric features such as, for example, notches, flats, bumps or raised regions. In an ultrasonic instrument according to the present invention, the balance portion generally extends from a node point on the ultrasonic transmission rod to the proximal end of the treatment portion. In an ultrasonic surgical instrument according to the present invention, the first and second balance asymmetries are positioned such that transverse vibrations in the ultrasonic transmission rod are substantially reduced and may be reduced to approximately zero. Further, in an ultrasonic surgical instrument according to the present invention, the balance ratio of the transmission waveguide may be reduced to less than 1:10 and may be further reduced to less than

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 6 is a side view of the balanced ultrasonic end effector illustrated in FIG. 5.

FIG. 7 is a top view of the balanced ultrasonic end effector illustrated in FIG. 5

DETAILED DESCRIPTION OF THE INVENTION

Figure 1:
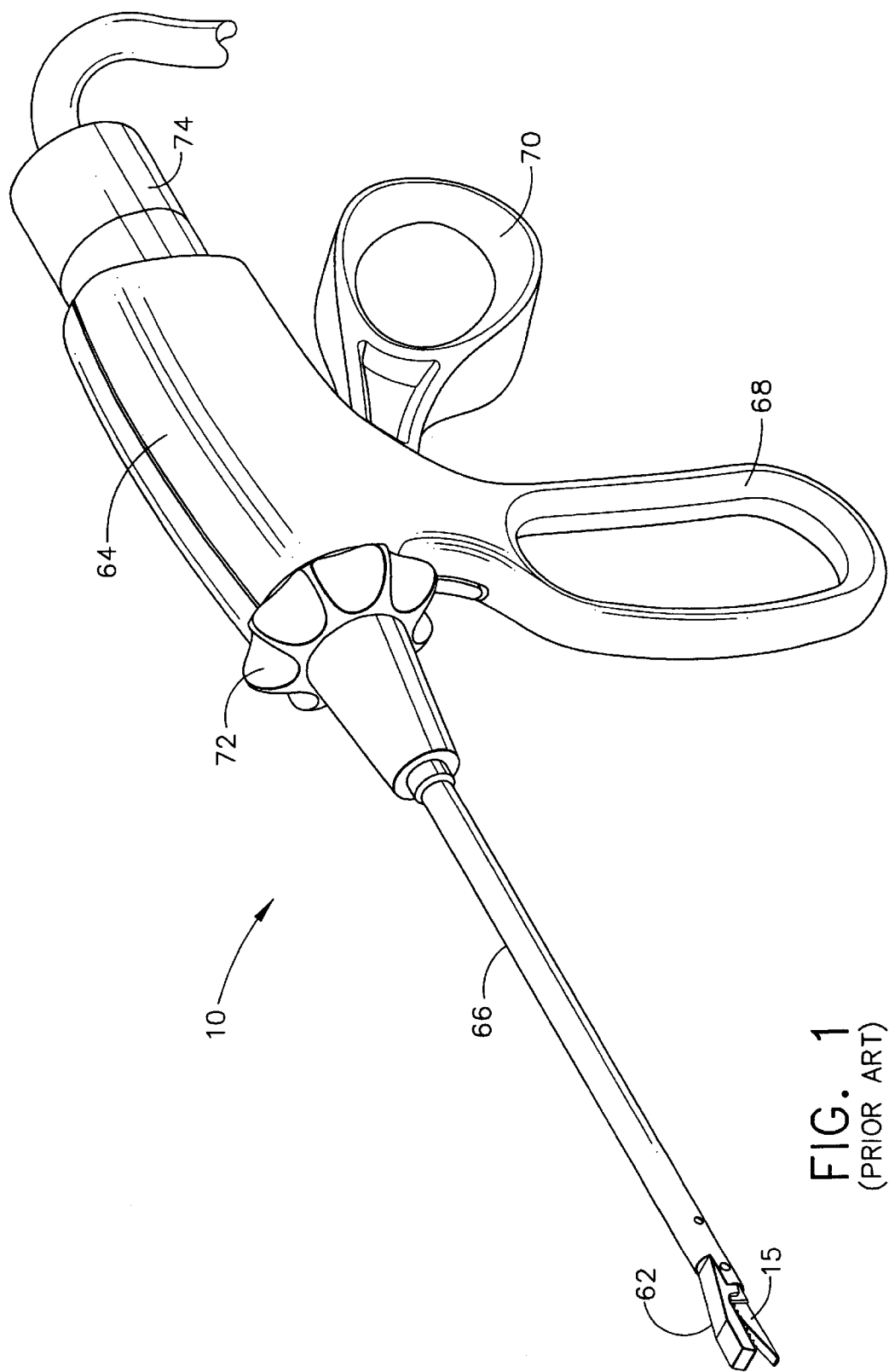
FIG. 1 is a perspective view of an ultrasonic surgical clamping instrument which incorporates a triangular end effector.

FIG. 1 is a perspective view of an ultrasonic surgical clamping instrument 10 which incorporates a triangular blade 15. In FIG. 1, clamping mechanism 62 and triangular ultrasonic blade 15 are supported and coupled to handle 64 by tube 66. Handle 64 includes finger grip 68, clamp trigger 70 and rotation knob 72. Handle 64 further includes an ultrasonic handpiece 74. Ultrasonic handpiece 74 is used to generate ultrasonic vibrations which are transmitted to triangular ultrasonic blade 15. Ultrasonic blade 15 is connected to ultrasonic handpiece 74 by an ultrasonic waveguide positioned in tube 66. Clamp trigger 70 is mechanically connected to clamping mechanism 62 such that distal movement of clamp trigger 70 forces clamping mechanism 62 to close against triangular ultrasonic blade 15. Triangular ultrasonic blade 15 is mechanically coupled to an ultrasonic transmission waveguide to form an ultrasonic transmission assembly. The ultrasonic transmission waveguide is positioned in tube 66 by, for example, o-rings and sealing rings.

Figure 2:
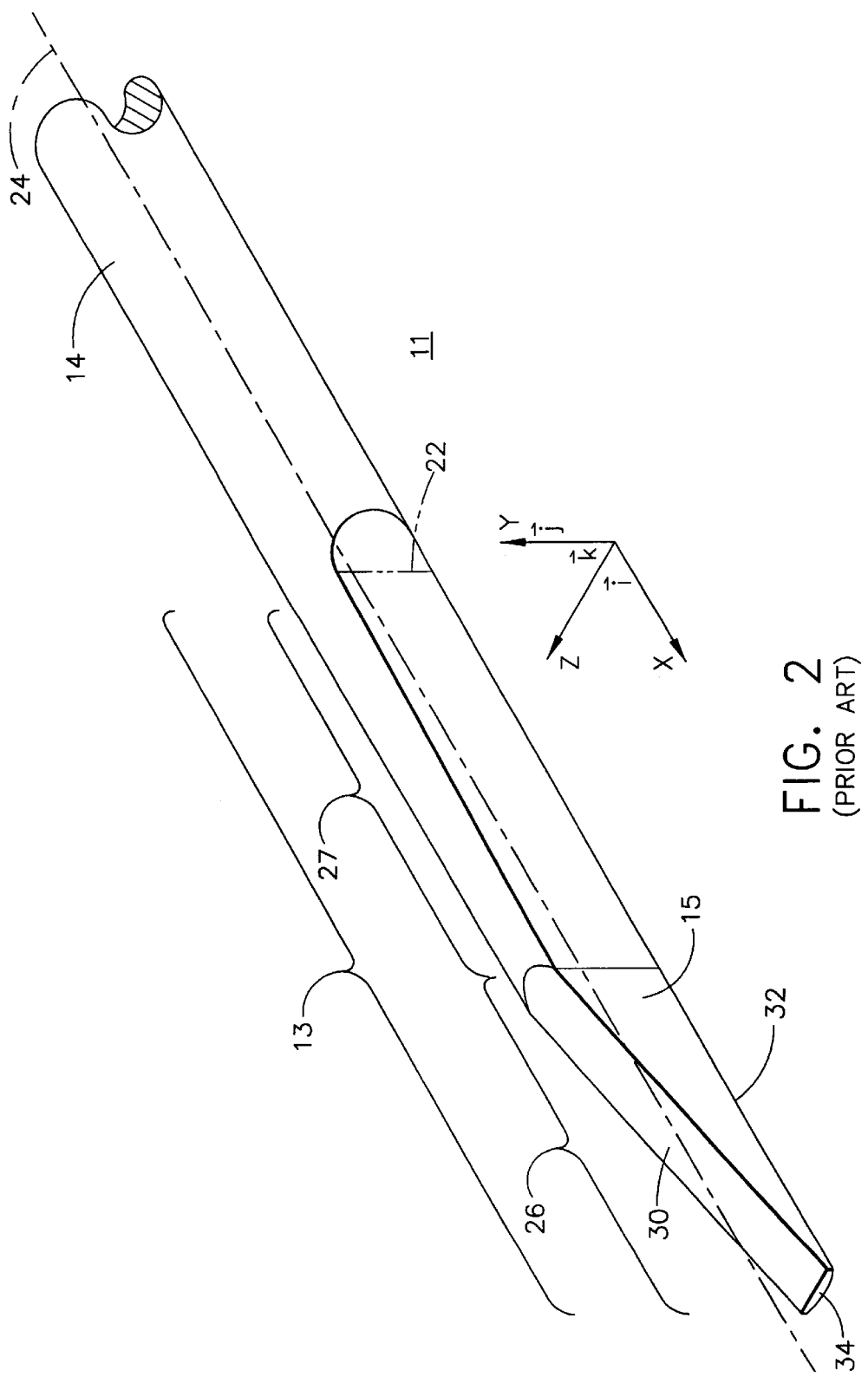
FIG. 2 is a perspective view of a prior art end effector.
Figure 3:
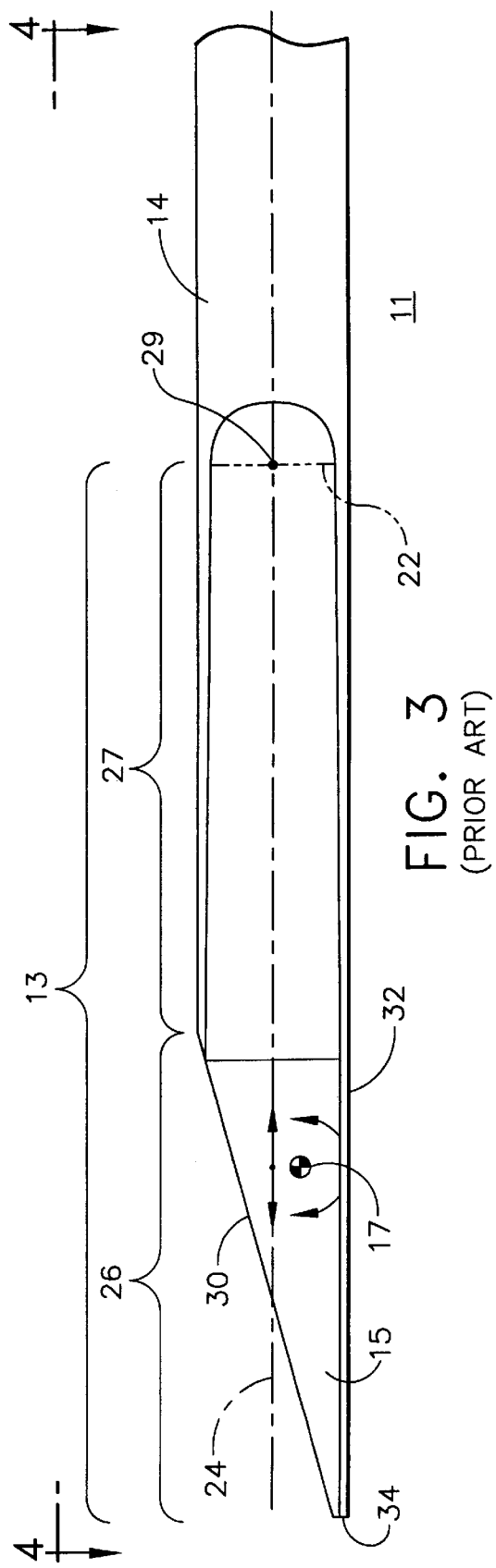
FIG. 3 is a side view of the prior art end effector illustrated in FIG. 2.
Figure 4:
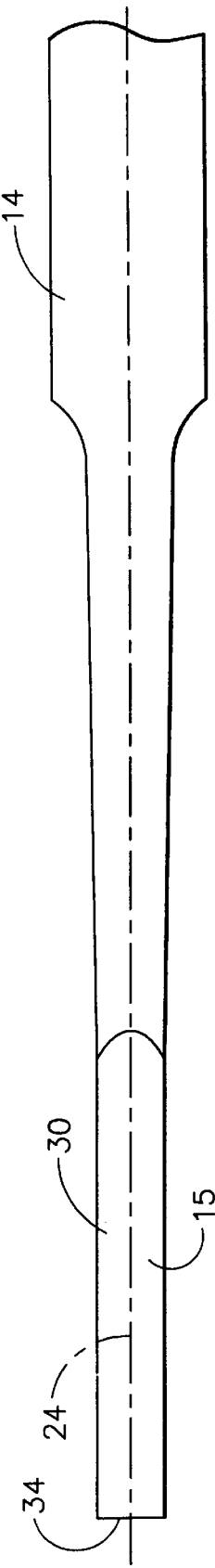
FIG. 4 is a top view of the prior art end effector illustrated in FIG. 2.

FIG. 2 is a perspective view of the distal end of ultrasonic transmission assembly 11, including end effector 13 which, in the instrument illustrated in FIGS. 2–4 is designed according to the prior art. FIG. 2 further includes an ordinate system in which: the x-axis lies along a central axis 24 of ultrasonic transmission waveguide 14 while the y-axis is the axis of asymmetry of a treatment region 26. End effector 13 is affixed to the distal end of transmission waveguide 14 at balance node 22. Central axis 24 of transmission waveguide 14 extends from the proximal end of transmission waveguide 14 to the distal end of transmission waveguide 14. Transmission waveguide 14 is generally symmetrical about central axis 24. End effector 13 includes treatment region 26, which is located at the distal end of end effector 13. Connector region 27 is located between treatment region 26 and balance node 22. Triangular ultrasonic blade 15 includes a blade surface 30 and a bottom surface 32. Treatment region 26 further includes rounded tip 34. FIG. 3 is a side view of prior art end effector 13. In FIG. 3, the shape of triangular ultrasonic blade 15 results in the center of mass 17 of triangular ultrasonic blade 15 being positioned away from waveguide central axis 24, resulting in an end effector 13 which is unbalanced and may, therefore, induce unwanted transverse motion in transmission waveguide 14. FIG. 4 is a top view of the prior art end effector 13.

Figure 5:
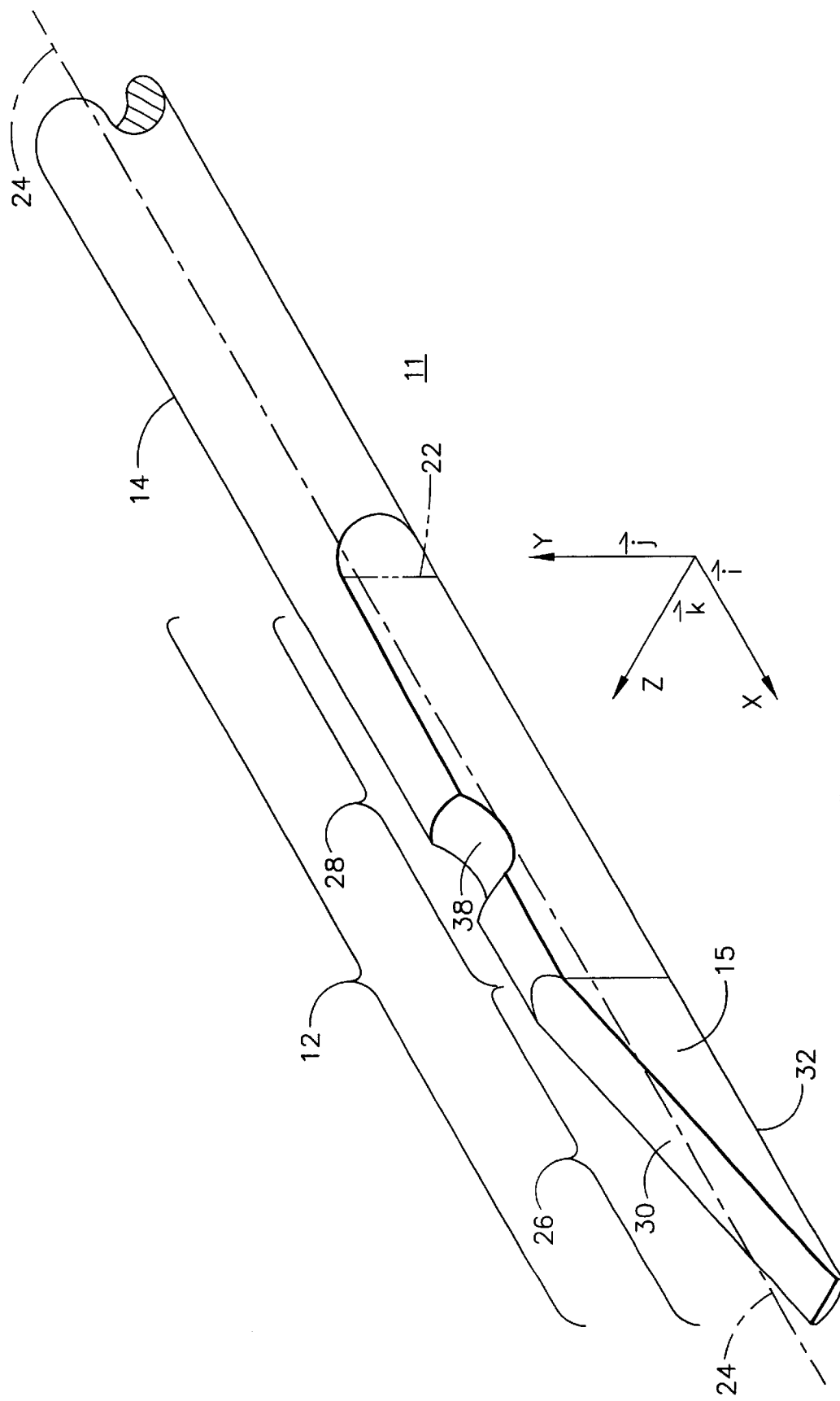
FIG. 5 is a perspective view of a balanced ultrasonic end effector according to the present invention.

FIG. 5 is a perspective view of the distal end, including balanced ultrasonic end effector 12, of an ultrasonic transmission assembly 11 according to the present invention. FIG. 5 further includes an ordinate system in which: the x-axis lies along a central axis 24 of ultrasonic transmission waveguide 14; and the y-axis is the axis of asymmetry of treatment region 26. End effector 12 is affixed to the distal end of transmission waveguide 14 at balance node 22. Central axis 24 of transmission waveguide 14 extends from the proximal end of transmission waveguide 14 to the distal end of transmission waveguide 14. Transmission waveguide 14 is substantially symmetrical about central axis 24. End effector 12 includes treatment region 26, which is located at the distal end of end effector 12. In the embodiment of FIGS. 5–12 treatment region 26 is triangular blade 15. End effector 12 further includes balance region 28, which is located between treatment region 26 and balance node 22. Triangular blade 15 includes a blade surface 30 and a bottom surface 32. In the illustrated embodiment of the invention, balance region 28 includes a first cutout 38 which act as an asymmetric balance feature by removing mass from the top of balance region 28. FIG. 6 is a side view of the distal end of ultrasonic transmission assembly 11 of FIG. 5, including balanced end effector 12. In FIG. 6, blade edge 30 extends from the proximal end of balance region 28 to tip 34. In FIG. 6, the addition of cutout 38 to balance region 28 balances end effector 12 even though center of mass 17 of triangular ultrasonic blade 15 is not on waveguide central axis 24. FIG. 7 is a top view of the balanced ultrasonic end effector 12 illustrated in FIG. 5.

Figure 8:
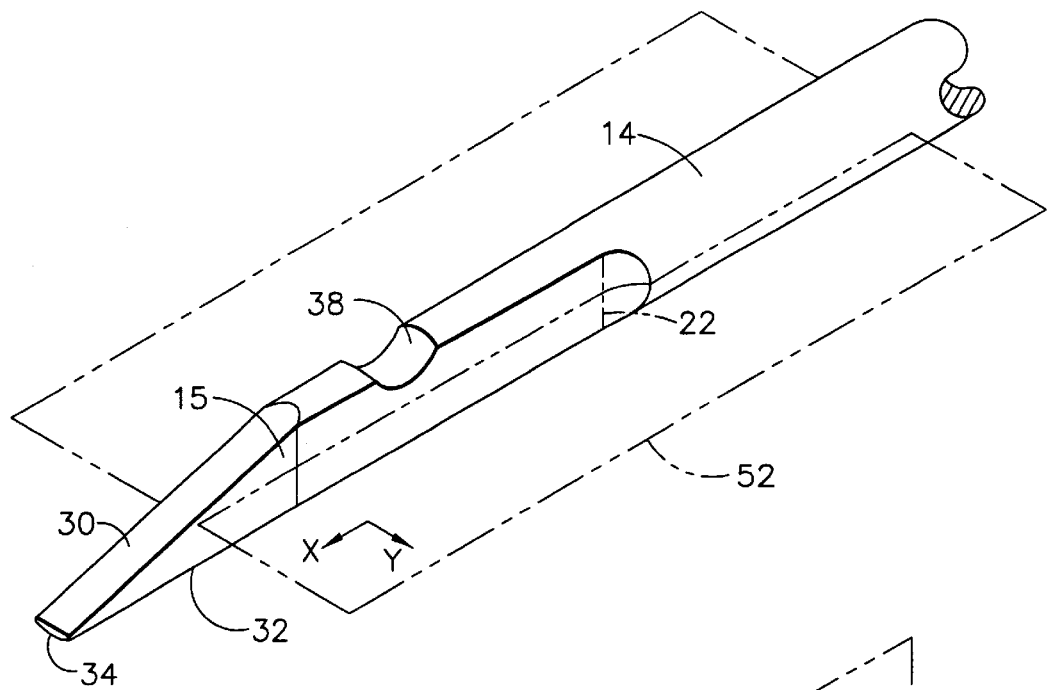
FIG. 8 is a perspective view of the balanced ultrasonic end effector illustrated in FIG. 5 with an x,y plane drawn through the center of the ultrasonic waveguide.

FIG. 8 is a perspective view of the distal end of ultrasonic transmission assembly 11 of the embodiment of the invention shown in FIG. 5 with a phantom x,y plane 52 drawn through the center of ultrasonic transmission waveguide 14. In FIG. 5, phantom x,y plane 52 passes through central axis 24 (not shown). Since blade surface 30 of treatment region 26 slopes away from x,y plane 52, end effector 12 is not symmetrical about x,y plane 52. Plane 52 may, therefore, be referred to as the plane of asymmetry for end effector 12.

Figure 9:
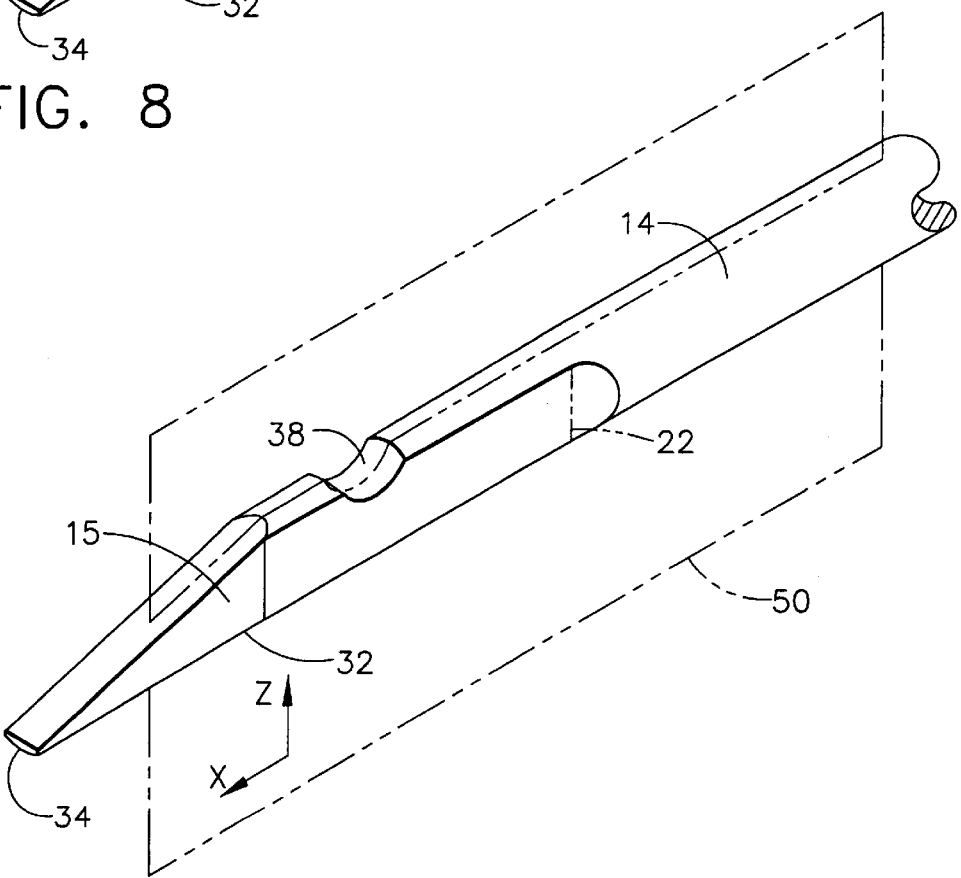
FIG. 9 is a perspective view of the balanced ultrasonic end effector illustrated in FIG. 5 with an x,z plane drawn through the center of the ultrasonic waveguide.

FIG. 9 is a perspective view of the distal end of the ultrasonic transmission assembly 11 of the embodiment of the invention shown in FIG. 5 with a phantom x,z plane 50 drawn through the center of ultrasonic transmission waveguide 14. In FIG. 6, phantom x,z plane 50 passes through central axis 24 (not shown) at an angle at 90° to x,y plane 52. End effector 12 is substantially symmetrical about plane 50. Plane 50 may, therefore, be referred to as the plane of symmetry for end effector 12.

Figure 10:
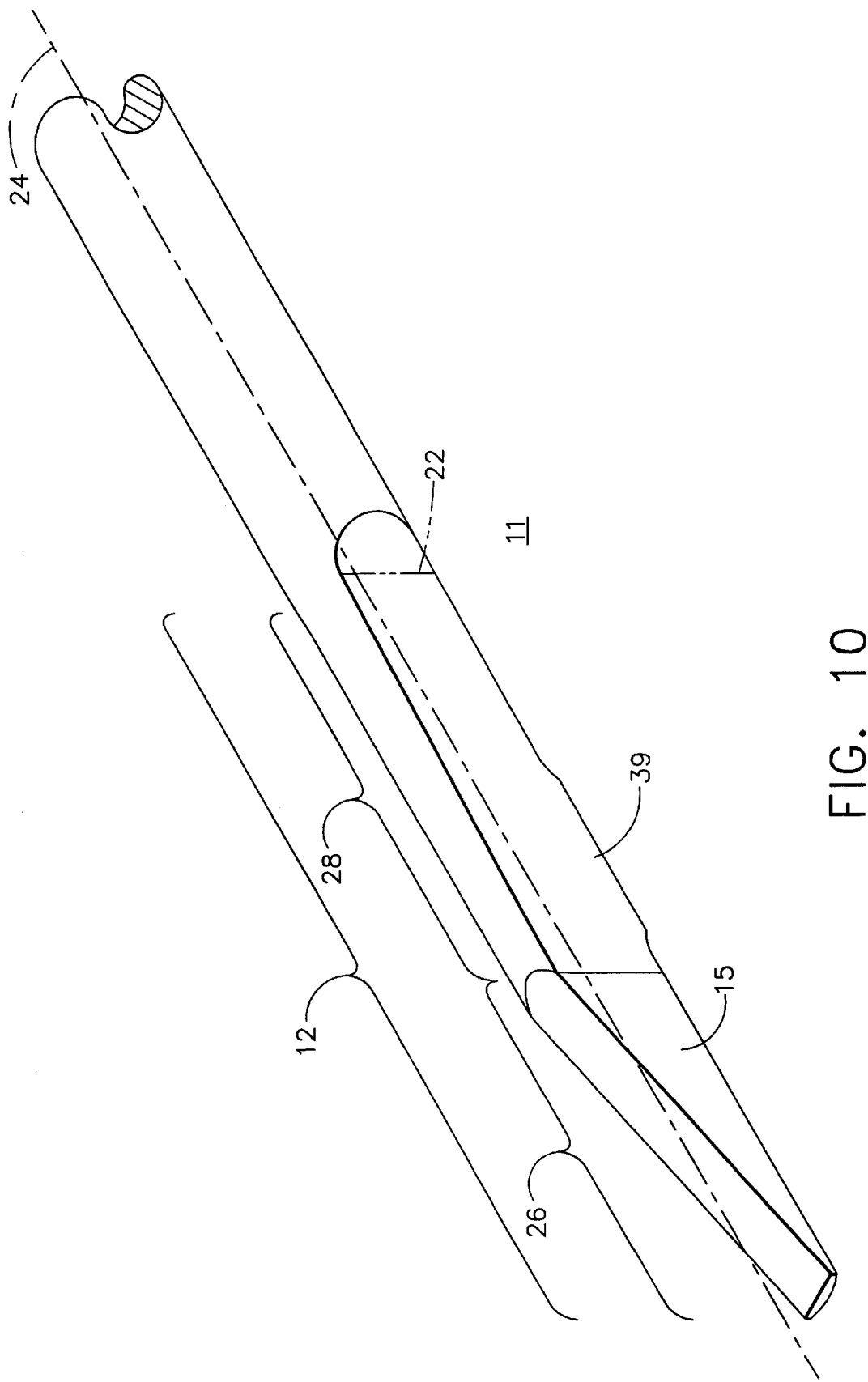
FIG. 10 is a perspective view of an alternate embodiment of a balanced ultrasonic end effector according to the present invention.
Figure 11:
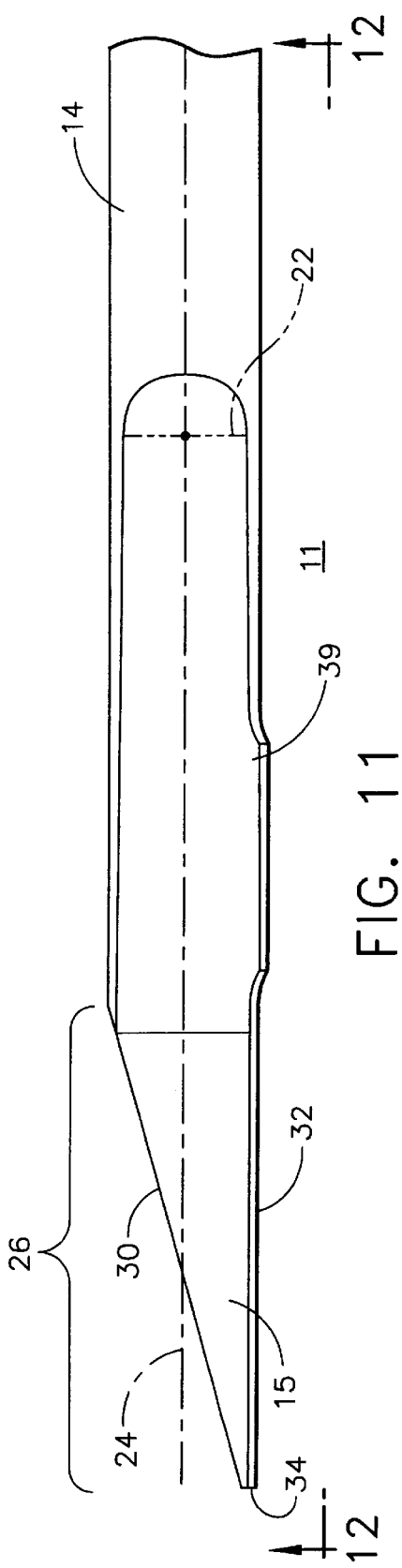
FIG. 11 is a side view of the balanced ultrasonic end effector illustrated in FIG. 10.
Figure 12:
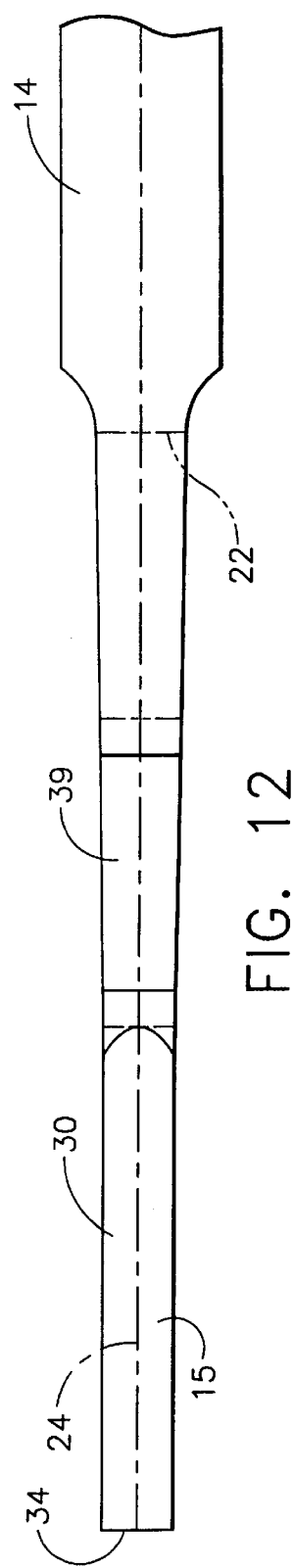
FIG. 12 is a bottom view of the balanced ultrasonic end effector illustrated in FIG. 11.

FIG. 10 is a perspective view of the distal end of an alternate embodiment of a balanced end effector 12 according to the present invention. In the embodiment of FIG. 10, raised region 39 balances end effector 12 by countering the effect of triangular ultrasonic blade 15. FIG. 11 is a side view of the end effector 12 illustrated in FIG. 10. FIG. 12 is a bottom view of the end effector 12 illustrated in FIG. 10.

Ultrasonic surgical instrument 10 has a treatment region 26 which includes a triangular blade designed to cut and coagulate tissue when vibrated at ultrasonic frequencies, such as, for example, fifty-five kilohertz (55 kHz). Triangular ultrasonic blade 15 in treatment region 26 is sloped to provide the surgeon with access and visibility when using ultrasonic instrument 10. Blade surface 30 of treatment region 26 may be sloped to facilitate use of a clamping mechanism with triangular ultrasonic blade 15 to provide a clamp coagulator instrument as illustrated in FIG. 1. As illustrated in FIGS. 8–9, triangular treatment region 26 is symmetrical about x,z plane 50 but is not symmetrical about x,y plane 52. When treatment region 26 is vibrated at an appropriate ultrasonic frequency to facilitate cutting and coagulation, the asymmetrical shape of treatment region 26 will tend to induce undesirable forces, including torque, which are transmitted back to transmission waveguide 14 and induce undesirable transverse vibrations in transmission waveguide 14.

As previously described, it is known that these undesirable transverse vibrations may be minimized and the end effector 12 balanced by designing the end effector such that the center of mass at any point along the end effector is positioned on or very near the central axis of the transmission waveguide. However, where, as in the present invention, the asymmetry (e.g. the triangular treatment region 26), causes the center of mass to diverge substantially from a line extending from the central axis of the transmission waveguide and the addition of balance features within the treatment region is undesirable, the blade must be balanced using an alternative method.

According to the present invention, end effector 12 is balanced by reducing or eliminating the torque induced in end effector 12 proximal to treatment region 26 as a result of including functional asymmetrical features such as cutout 38 or raised region 39 in treatment region 26. A convenient physical point of reference at the proximal end of end effector 12 is balance node 22. It should be noted that balance node 22 may be any node of longitudinal vibration along transmission waveguide 14 and is not necessarily the most distal vibratory node. Nodes of longitudinal vibration occur at half wavelength intervals along the transmission waveguide, wherein the wavelength of interest is the wavelength of the frequency at which the ultrasonic end effector is driven (e.g. approximately 55 kHz). In the embodiment of the invention illustrated herein, the asymmetric functional features comprise triangular ultrasonic blade 15. A feature is asymmetric when its cross-section is not symmetric with respect to waveguide central axis 24. A feature is symmetric when its cross-section is symmetric with respect to waveguide central axis 24. That is, a feature is symmetric when a chord through a cross-section of the portion of the end effector which includes the feature is bisected by central axis 24.

According to the present invention, a balance region 28 is included in end effector 12 and end effector 12 is balanced by positioning an asymmetric balance feature in balance region 28 between the proximal end of treatment region 26 and balance node 22. The size, shape and position of the asymmetric balance feature included in balance region 28 are selected to reduce the torque at a balance point 29 to zero or as close to zero as possible. Balance point 29 is on central axis 24 positioned at, for example, balance node 22. The degree to which the torque at balance point 29 is reduced will depend upon particular design and manufacturing constraints. Thus, by appropriately arranging an asymmetric balance feature in balance region 28, the torque induced by the asymmetric functional features in treatment region 26 may be canceled by the torque induced by the asymmetric balance feature. With the summation of torsional forces distal to end effector 12 minimized, the transverse vibration induced in transmission waveguide 14 will be substantially reduced and may be reduced to approximately zero.

In order to determine whether an asymmetric end effector has been properly balanced, it may be appropriate to measure the torque induced in transmission waveguide 14. The relative magnitude of the torque induced in transmission waveguide 14 may be estimated by taking the ratio of the peak lateral displacement, less Poisons swelling (also referred to as longitudinal node swelling), at any transverse vibratory antinode of the transmission waveguide to the peak longitudinal displacement at any longitudinal vibratory antinode of the transmission waveguide. The closer the ratio is to zero, the less transverse vibration is being induced in the waveguide. Thus, the ratio of peak lateral displacement to peak longitudinal displacement may be referred to as the "balance ratio". In one embodiment of the present invention, a blade would be considered balanced if the balance ratio of peak lateral displacement to peak longitudinal displacement is 1:10 or less. More particularly, using the techniques described herein, it may be possible to achieve balance ratios of 1:200 or less.

An asymmetric feature is a feature of the end effector wherein the center of mass of the feature is off a line extending from the central axis of the transmission waveguide. In an end effector having a symmetrical orientation and an asymmetrical orientation, such as the end effector illustrated in the Figures, all of the asymmetric features are in a plane parallel to the plane of symmetry.

The mass and shape of the asymmetric balance feature introduced into balance region 26 are determined by a number of factors. The torque induced at balance point 29 is equal to the integral over volume of the cross product of the vector acceleration at each point on the end effector with a position vector multiplied by a density scalar. The density scaler is a function which represents the density of the end effector at each point on the end effector. Expressing that equation mathematically, the torque ($\vec{T}$) at balance point 29 is $$\int_{x_0}^{x_1}\int_{y_0}^{y_1}\int_{z_0}^{z_1} \vec{A}(x, y, z) \times \vec{o}(x, y, z)\rho(x, y, z)dzdydx, \qquad (1)$$

where:

$x_0$, $y_0$, and $z_0$ are located in the plane x=0 at balance point 29;

$x_1$, $y_1$, and $z_1$ are located in a plane tangential to the distal tip of end effector 12 and, with $x_o$, $y_o$, and $z_o$, define a region which encloses end effector 12;

$\vec{A}(x,y,z)$ is the acceleration of the blade at any point (x,y,z);

$\vec{o}(x,y,z)$ is a vector indicative of the position of the point (x,y,z) with respect to balance point 29; and (x,y,z) is the density of the blade at any point (x,y,z).

Therefore, in a balanced end effector designed according to the present invention, an end effector 12 is designed to incorporate one or more beneficial asymmetries in treatment region 26 (e.g. triangular blade 15). A balance node point is then selected at a convenient vibratory node along waveguide 14. Normally the balance node point will be the most distal vibratory node on waveguide 14. A symmetrical (e.g. cylindrical) balance region 28 is then incorporated into end effector 12. In the illustrated embodiments, balance region 28 extends from balance node 22 to the proximal end of treatment region 26. Normally the proximal end of treatment region 26 will correspond with the proximal end of the proximal most beneficial asymmetry. For example, in the embodiment of the invention illustrated in FIG. 2, the proximal end of treatment region 26 corresponds to the proximal end of curved blade edge 36. Once the appropriate beneficial asymmetries have been designed into the end effector, the torque induced at balance point 29 by the end effector design, including beneficial asymmetries. may be calculated using Equation (1) above.

In using Equation (1) above to calculate the torque induced by any particular asymmetry at balance point 29, a suitable first step is to find a mathematical expression for $\vec{A}(x,y,z)$, the acceleration at each point along end effector 12, along with a mathematical expression for p(x,y,z), the density at each point along end effector 12, and a mathematical expression for $\vec{o}(x,y,z)$, the position vector for each point along end effector 12 with respect to balance point 29. For convenience, $\vec{o}(x,y,z)$ may be referred to as the offset vector. As Equation (1) indicates, the torque induced at balance point 29 by end effector 12 is the volume integral of the cross product of the acceleration vector with the product of the offset vector and scalar density. In Equation (1), the integral is taken over the volume of the end effector. Generally stated, the torque induced at balance point 29 will be equal to the sum of the torques induced by each asymmetry in end effector 12. Thus an optimum design may be obtained where a balance asymmetry is incorporated into balance region 28 such that the torque induced by the balance asymmetry cancels the torque induced by the beneficial asymmetry.

In an ideal situation it would be possible to express $\vec{A}(x,y,z)$, $\vec{o}(x,y,z)$, and p(x,y,z) using mathematical formulas which could be conveniently integrated over the volume of end effector 12. However, it is generally very difficult to develop such mathematical formulas for ultrasonic surgical end effector geometry because ultrasonic surgical end effectors do not generally assume continuous geometric shapes such as cones or cylinders. Therefore, once the variables have been calculated or modeled, the integral may be calculated using, for example, a numerical integration program. Of the parameters $\vec{A}(x,y,z)$, $\vec{o}(x,y,z)$, and p(x,y,z), the most difficult to calculate is generally the acceleration vector $\vec{A}(x,y,z)$ for each point along end effector 12, particularly for end effectors having complex geometry. Therefore, it is usually necessary to use methods other than direct calculation to obtain an approximation of the acceleration at any point along end effector 12. For example, the displacement at each point may be a suitable approximation of the acceleration with a suitable scaling factor. Displacement may be calculated using, for example, finite element analysis of the blade. Alternatively, velocity at each point may be used to obtain an estimate of acceleration at a given frequency. The velocity at specific points may be calculated by, for example, physically observing external points along the blade surface, (e.g. using a laser vibrometer) and assuming that the interior points are acting in the same manner as the surface points. As another example, the velocity of any point along the blade may be approximated as substantially sinusoidal function of the distance from the balance node point.

The calculation of position vector $\vec{o}(x,y,z)$ is generally tied to the method used to calculate $\vec{A}(x,y,z)$. For example, if $\vec{A}(x,y,z)$ is measured or approximated at specific points along the end effector, then $\vec{o}(x,y,z)$ would be the position vector taken at those specific points.

Since ultrasonic instruments according to the present invention normally utilize end effectors constructed of titanium, aluminum or an alloy of titanium or aluminum the density at any point p(x,y,z) is a constant. Therefore, in general p(x,y,z)=P where P is the density of the material used in the end effector.

In practice, an end effector is designed which incorporates suitable beneficial asymmetries into treatment region 26. Those beneficial asymmetries induce an undesirable torque $\vec{T}_u$ at balance point 29 which may be calculated using Equation (1). Once the undesirable torque $\vec{T}_u$ for a particular design is known, a balance asymmetry may be added in balance region 28 to generate a balance torque $\vec{T}_b$ at balance point 29 which cancels the undesirable torque $\vec{T}_u$ generated by the beneficial asymmetries. Adding a balance asymmetry to balance region 28 consists of adding or subtracting mass from particular portions of balance region 28. The size and position of the mass added or subtracted is determined not only by the balance torque $\vec{T}_b$ induced at balance point 29 but also by considerations such as the effect upon the look, feel and ergonomics of the end effector. Therefore, once $\vec{T}_u$ is calculated, the designer may begin to add and subtract mass from balance region 28 to create a balance asymmetry which induce a beneficial torque at balance point 29.

It may be possible to simplify the calculations required. For example, using suitable assumptions, it is possible to simplify Equation (1) for the purpose of calculating $\vec{T}_b$. In particular, by assuming that the balance asymmetry can be modeled as a series of point masses and neglecting the effect of rotation:

$$\vec{T}_b = m\vec{A}_s \times \vec{o}_{CM_m} \quad (2)$$

where: m is the mass of the balancing feature;

$\vec{T}_b$ is the torque induced at balance point 29 by the balance asymmetry designed into balance region 26;

$\vec{A}_s$ is the average or a representative vector acceleration at the point in balance region 26 where mass is added; and $\vec{o}_{CM_m}$ is an offset vector pointing to the Center of Mass of mass n.

By designing the balance asymmetry to be symmetrical about plane of symmetry 50, the torque exerted at node 22 may be modeled as being entirely about the z-axis of the end effector. If the balance asymmetry is located on a plane of symmetry 50, equation (2) becomes:

$$\vec{T}_b = m\vec{A}_s \times \vec{o}_{CM_m} \quad (3)$$

or, $$\vec{T}_b \cdot \vec{k} = m\vec{A}_s \times \vec{o}_{CM_m} \cdot \vec{k} \quad (4)$$

or, neglecting signs, $$|\vec{T}_b| = |m\vec{A}_s \times \vec{o}_{CM_m}| \quad (5)$$

It will be apparent that a significant number of combinations of balance asymmetry sizes and shapes may be used to generate an appropriate torque $\vec{T}_b$ at balance node 29. Further, the size and shape of a particular balance asymmetry chosen will be a function of the material used to create that asymmetry. Therefore, the designer is normally left to select a balance asymmetry which not only generate the desired balance torque $\vec{T}_b$, but meet other design criteria as well. Further, as mass is added to or removed from balance region 28 the stiffness (and thus the vibrational characteristics) of the system changes. For example, the system stiffness would generally increase with added mass and decrease when mass is removed. Thus, the actual design of an appropriate balance asymmetry becomes an iterative exercise, with the blade designer selecting preferred shapes and positions for the balance asymmetry then checking those shapes and positions using one of Equation (1), (2) or (5). The shape and size of the balance asymmetry may be adjusted as required to generate $\vec{T}_b$.

An end effector according to the present invention may also be designed using one or more empirical methods such as, for example, using modal analysis. In the empirical methods, the end effector is designed with appropriate beneficial asymmetries included in treatment region 26. Balance region 28 is then modeled as a symmetric connector between the treatment region and transmission waveguide 14. Since treatment region 28 includes beneficial asymmetries (e.g. curved blade edges 36) without a corresponding balance asymmetry in balance region 28, this first pass end effector will tend to be unbalanced. Once a first pass end effector is developed, a suitable measurement of the torque generated at a preselected point, such as balance point 29, may be selected. For example, the balance ratio of peak lateral displacement to peak longitudinal displacement as measured in the transmission waveguide. The first pass end effector may then be numerically modeled and vibrated using modal analysis or finite element analysis techniques. With the first pass numerical model driven at a suitable generator frequency (e.g. 55 kHz), it is possible, using, for example, finite element analysis programs, to determine the ratio of peak lateral displacement to peak longitudinal displacement at selected points along the transmission waveguide. The end effector may then be balanced (i.e. the ratio of peak lateral displacement to peak longitudinal displacement reduced to less than 1:10) by adding or subtracting mass in the balance region. This is, of course, an iterative process which may be enhanced (i.e. fewer iterations required) by the skill and experience of the designer.

A further empirical design technique involves designing a first pass end effector in the manner set forth above. A physical model of the first pass end effector is then built and tested by driving the input of the transmission waveguide at a suitable generator frequency. The frequency at which the end effector is driven may be referred to as the drive frequency. With the first pass end effector driven at the drive frequency, a suitable measurement of the torque generated at the balance node may be selected, for example, the balance ratio can be measured directly from the transmission waveguide. The end effector may then be balanced (i.e. the balance ratio reduced to less than 1:10) by physically adding or subtracting mass in the balance region. This is, of course, an iterative process which may be enhanced (i.e. fewer iterations required) by the skill and experience of the designer. No matter the design method chosen, whether empirical or analytical, if it is an iterative process, the rougher the first approximation used, the more iterations will be necessary to arrive at balanced blade design.

As described herein, balance node 22 was selected as the proximal origin of balance region 26 in order to provide clarity and to set forth a physically definable point of reference which may be located on any transmission waveguide, using either mathematical computation or physical measurements. As it happens, using node 22 as the proximal origin of balance region 26 is also beneficial in that it is believed to make the mathematics set forth herein cleaner and more understandable. However, it should be recognized that using the present invention, the undesirable torque generated in the waveguide will be substantially canceled by the balance torque generated in the waveguide from a point just proximal to the balance asymmetry. For example, in the embodiment of the invention illustrated in FIG. 5, the torque will converge to substantially zero in the portion of the waveguide proximal to cutout 38.

While the embodiments illustrated and described herein have a beneficial asymmetry in only one direction, the present technique may be beneficial in balancing blades having beneficial asymmetries in any two or more directions. It will be apparent that, in a balanced surgical end effector designed according to the present invention, the center of mass of the end effector may not be positioned on the central axis of the waveguide. A blade, according to the present invention, may also be designed to include a blunt or a sharp edge. A balanced ultrasonic blade designed, according to the present invention, may be used to perform many open and endoscopic surgical procedures, including: internal mammary artery (IMA) takedown procedures; removal or dissection of the radial artery; breast reduction and reconstruction; and hemorrhoid removal. While the present invention is described with respect to a triangular blade, the techniques described herein may be effectively used to balance curved or other irregularly shaped blades.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An end effector for use in an ultrasonic surgical instrument, wherein said end effector comprises:
    an ultrasonic transmission rod having a proximal end and a distal end;
    an ultrasonically actuated blade attached to said distal end of said transmission rod, wherein said ultrasonically actuated blade comprises:
        a distal end;
        a proximal end connected to said transmission rod at a longitudinal vibratory node point;
        a treatment portion including at least one functional asymmetry; and
        a balance portion including a singular balance asymmetry wherein said balance portion extends from said node point to said treatment portion and said treatment portion extends from said balance portion to said distal end of said blade.

2. An end effector according to claim 1, wherein said balance asymmetry is positioned to counter torque created at said proximal end of said blade by said at least one functional asymmetry.

3. An end effector according to claim 2, wherein said balance asymmetry is positioned such that transverse vibrations in said ultrasonic transmission rod are substantially equal to zero.

4. An end effector according to claim 2 wherein said transmission rod has a balance ratio of less than 1:10.

5. An end effector according to claim 4 wherein said balance ratio of said transmission rod is less than 1:200.

6. An end effector for use in an ultrasonic surgical instrument, wherein said end effector comprises:
   an ultrasonic transmission rod having a proximal end and a distal end;
   a balanced ultrasonically actuated blade attached to said distal end of said transmission rod, wherein said balanced ultrasonically actuated blade comprises:
   a distal end;
   a proximal end;
   an angled treatment portion; and
   a balance portion including a singular balance asymmetry wherein said balance portion extends from said distal end of said ultrasonic waveguide to said treatment portion and said treatment portion extends from said balance portion to said distal end of said blade.

7. An end effector according to claim 6 wherein said blade has a top surface and a bottom surface, said top surface including said angled treatment portion and said bottom surface being parallel to said transmission rod, said first singular balance asymmetry being positioned on said top surface.

8. An end effector according to claim 7 wherein said singular balance asymmetry comprises a cutout on said top surface of said balance portion.

9. An end effector according to claim 7 wherein said singular balance asymmetry comprises a raised region on said bottom surface of said balance region.

10. An end effector according to claim 8 wherein said blade is bisected by a plane of symmetry, said blade being substantially symmetrical on either side of said plane of symmetry, said singular balance asymmetry comprising a cutout on said top surface of said blade wherein said cutout is substantially parallel to said plane of symmetry and wherein said cutout is substantially symmetrical on either side of said plane of symmetry.

11. An end effector according to claim 9 wherein said blade is bisected by a plane of symmetry, said blade being substantially symmetrical on either side of said plane of symmetry, said singular balance asymmetry comprising a raised region positional on said bottom surface of said blade, wherein said raised region is substantially parallel to said plane of symmetry and wherein said raised region is substantially symmetrical on either side of said plane of symmetry.

12. An ultrasonic surgical instrument including a balanced end effector for, wherein said instrument comprises:
   a handle including an ultrasonic handpiece;
   an ultrasonic transmission rod having a proximal end and a distal end wherein said proximal end is operatively connected to said handpiece;
   an ultrasonically actuated blade attached to said distal end of said transmission rod, wherein said ultrasonically actuated blade comprises:
   a distal end;
   a proximal end connected to said transmission rod at a longitudinal vibratory node point;
   a treatment portion including at least one functional asymmetry; and
   a balance portion including a singular balance asymmetry wherein said balance portion extends from said node point to said treatment portion and said treatment portion extends from said balance portion to said distal end of said blade.

13. An ultrasonic surgical instrument according to claim 12, wherein said balance asymmetry is positioned to counter torque created at said proximal end of said blade by said at least one functional asymmetry.

14. An ultrasonic surgical instrument according to claim 13, wherein said balance asymmetry is positioned such that transverse vibrations in said ultrasonic transmission rod are substantially equal to zero.

15. An ultrasonic surgical instrument according to claim 13, wherein said transmission rod has a balance ratio of less than 1:10.

16. An ultrasonic surgical instrument according to claim 15 wherein said balance ratio of said transmission rod is less than 1:200.

17. An ultrasonic surgical instrument, comprising:
   a handle
   an ultrasonic transmission rod having a proximal end and a distal end wherein said proximal end is operatively connected to said handle;
   a balanced ultrasonically actuated blade attached to said distal end of said transmission rod, wherein said balanced ultrasonically actuated blade comprises:
   a distal end;
   a proximal end;
   an angled treatment portion; and
   a balance portion including a singular balance asymmetry wherein said balance portion extends from said distal end of said ultrasonic waveguide to said treatment portion and said treatment portion extends from said balance portion to said distal end of said blade.

18. An ultrasonic surgical instrument according to claim 17 wherein said blade has a top surface and a bottom surface, said top surface including said angled treatment portion and said bottom surface being parallel to said transmission rod, said singular balance asymmetry being positioned on said top surface.

19. An ultrasonic surgical instrument according to claim 18 wherein said singular balance asymmetry comprises a cutout on said top surface of said balance portion.

20. An ultrasonic surgical instrument according to claim 18 wherein said singular balance asymmetry comprises a raised region on said bottom surface of said balance portion.

21. An end effector according to claim 19 wherein said blade is bisected by a plane of symmetry, said blade being substantially symmetrical on either side of said plane of symmetry, said singular balance asymmetry comprising a cutout on said top surface of said blade wherein said cutout surface is substantially parallel to said plane of symmetry and wherein said cutout is substantially symmetrical on either side of said plane of symmetry and wherein said cutout is substantially symmetrical on either sides of said plane of symmetry.

22. An ultrasonic surgical instrument according to claim 20 wherein said blade is bisected by a plane of symmetry, said blade being substantially symmetrical on either side of said plane of symmetry, said singular balance asymmetry comprising a raised region positional on said bottom surface of said blade, wherein said raised region is substantially parallel to said plane of symmetry and wherein said raised region is substantially symmetrical on either side of said plane of symmetry.

* * * * *